United States Patent
Yoo et al.

(10) Patent No.: US 10,718,912 B2
(45) Date of Patent: Jul. 21, 2020

(54) ANNULAR-BEAM COUPLING SYSTEM

(71) Applicant: INDUSTRY-UNIVERSITY COOPERATION FOUNDATION HANYANG UNIVERSITY, Seoul (KR)

(72) Inventors: Hong Ki Yoo, Seoul (KR); Min Woo Lee, Suwon-si (KR); Jingchao Xing, Seoul (KR)

(73) Assignee: INDUSTRY-UNIVERSITY COOPERATION FOUNDATION HANYANG UNIVERSITY, Seoul (KR)

(*) Notice: Subject to any disclaimer, the term of this patent is extended or adjusted under 35 U.S.C. 154(b) by 0 days.

(21) Appl. No.: 16/322,685

(22) PCT Filed: May 16, 2018

(86) PCT No.: PCT/KR2018/005592
§ 371 (c)(1),
(2) Date: Feb. 1, 2019

(87) PCT Pub. No.: WO2018/216946
PCT Pub. Date: Nov. 29, 2018

(65) Prior Publication Data
US 2019/0346636 A1   Nov. 14, 2019

(30) Foreign Application Priority Data

May 26, 2017 (KR) ........................ 10-2017-0065090

(51) Int. Cl.
G02B 6/32 (2006.01)
G02B 6/42 (2006.01)
(Continued)

(52) U.S. Cl.
CPC ........... *G02B 6/4206* (2013.01); *G02B 6/032* (2013.01); *G02B 6/03611* (2013.01)

(58) Field of Classification Search
CPC ...... G02B 6/32; G02B 6/4214; G02B 6/4204; G02B 6/4292; G02B 6/4249
See application file for complete search history.

(56) References Cited

U.S. PATENT DOCUMENTS 5,199,431 A    4/1993 Kittrell et al.
8,592,768 B1 * 11/2013 Djeu .................. G01N 21/3151
                                                    250/339.12
(Continued)

FOREIGN PATENT DOCUMENTS

FR    2490045 A1 *   3/1982   ........... G02B 6/4246
JP    2000-047038 A   2/2000
(Continued)

*Primary Examiner* — Jennifer Doan

(57) ABSTRACT

Disclosed is an annular-beam coupling system enabling reduction of noise generated from a core of a double-clad fiber. The disclosed annular-beam coupling system comprises: a fiber for transmitting light of a light source; a collimator for receiving the light outputted from the fiber and forming a parallel beam of a circular shape; an annular-beam generation unit for converting the parallel beam into an annular beam; and a double-clad fiber having the annular beam coupled to a cladding region thereof.

7 Claims, 9 Drawing Sheets

(51) Int. Cl.
   *G02B 6/032*   (2006.01)
   *G02B 6/036*   (2006.01)

(56) References Cited

U.S. PATENT DOCUMENTS

| | | |
|---|---|---|
| 2004/0254474 A1 | 12/2004 | Seibel et al. |
| 2009/0024191 A1* | 1/2009 | Seibel ................ A61B 1/0008 607/92 |
| 2015/0234195 A1* | 8/2015 | Honea ................ G02B 27/0927 359/618 |

FOREIGN PATENT DOCUMENTS

| | | |
|---|---|---|
| JP | 2009-528128 A | 8/2009 |
| KR | 10-2013-0035254 A | 4/2013 |

\* cited by examiner

FIB. 5B refractive indexes
$n_2 > n_3 > n_1$

ANNULAR-BEAM COUPLING SYSTEM

CROSS-REFERENCE TO RELATED APPLICATIONS

This application is a National Stage Entry of PCT International Application No. PCT/KR2018/005592, which was filed on May 16, 2018, and which claims priority from Korean Patent Application No. 10-2017-0065090 filed with the Korean Intellectual Property Office on May 26, 2017. The disclosures of the above patent applications are incorporated herein by reference in their entirety.

BACKGROUND

1. Technical Field

The present disclosure relates to an annular-beam coupling system, more particularly to an annular-beam coupling system capable of reducing noise generated in the core of a double-clad fiber.

2. Description of the Related Art

The related art associated with the imaging catheter, which is used for diagnosing cardiovascular diseases, etc., includes ultrasonic techniques, near-infrared imaging techniques, optical coherence tomography techniques, etc., where many such techniques have been commercialized and are being utilized in clinics.

Ultrasonic techniques, which involve inserting a device in the form of a catheter into a sample such as a blood vessel, etc., to obtain cross-sectional images of the blood vessel, are still the most widely utilized in hospitals for intravascular imaging. Since ultrasonic technology is used, the resolution is low, at a level of about 100 µm, the contrast is low also, and the imaging speed is slow, at about 30 seconds.

Near-infrared imaging techniques may involve identifying whether or not there are lipids in the inner walls of a blood vessel via a spectroscopic method using near-infrared light, and recently, a near-infrared imaging technique was combined with an intravascular ultrasonic technique to be implemented in a single catheter.

Optical coherence tomography (OCT) techniques, similar to intravascular ultrasonic techniques, involve inserting a device in the form of a catheter into a blood vessel to emit light into the blood vessel and obtaining tomographic images of the blood vessel by analyzing the returning light. The microscopic structures of living tissue may be acquired based on a combination of the principles of white light interferometry and confocal microscopy.

Also, optical coherence tomography techniques are being combined with near-infrared fluorescence imaging or near-infrared spectroscopy in implementations for imaging catheter systems.

SUMMARY

An aspect of the present disclosure is to provide an annular-beam coupling system that is capable of reducing noise that occurs in the core of a double-clad fiber.

To achieve the objective above, an embodiment of the present disclosure provides an annular-beam coupling system that includes: a fiber configured to transfer light from a light source; a collimator configured to receive the light outputted from the fiber and form a parallel beam of a circular shape; an annular-beam generation unit configured to convert the parallel beam into an annular beam; and a double-clad fiber configured such that the annular beam is coupled to its cladding region.

Also, another embodiment of the present disclosure, to achieve the objective above, provides an annular-beam coupling system that includes: a light source; a multi-mode fiber configured to guide light from the light source; and a double-clad fiber configured such that an annular beam outputted from the multi-mode fiber is coupled to its cladding region, where the light from the light source enters the multi-mode fiber such as to be guided in the core's perimeter region, which is separated from a central axis of the multi-mode fiber by a preset distance.

Yet another embodiment of the present disclosure, to achieve the objective above, provides an annular-beam coupling system that includes: a light source; a hollow core fiber configured to receive light from the light source and output an annular beam; and a double-clad fiber configured such that the annular beam is coupled to its cladding region.

According to an embodiment of the present disclosure, the annular beam can be coupled to the cladding region of a double-clad fiber without being coupled to the core, whereby noise components such as autofluorescence components, Raman scattering signals, etc., generated in the core of the double-clad fiber can be reduced.

BRIEF DESCRIPTION OF THE DRAWINGS

FIG. 5A, FIG. 5B and FIG. 6 illustrate examples of a phase spatial filter.

DETAILED DESCRIPTION

Figure 1:
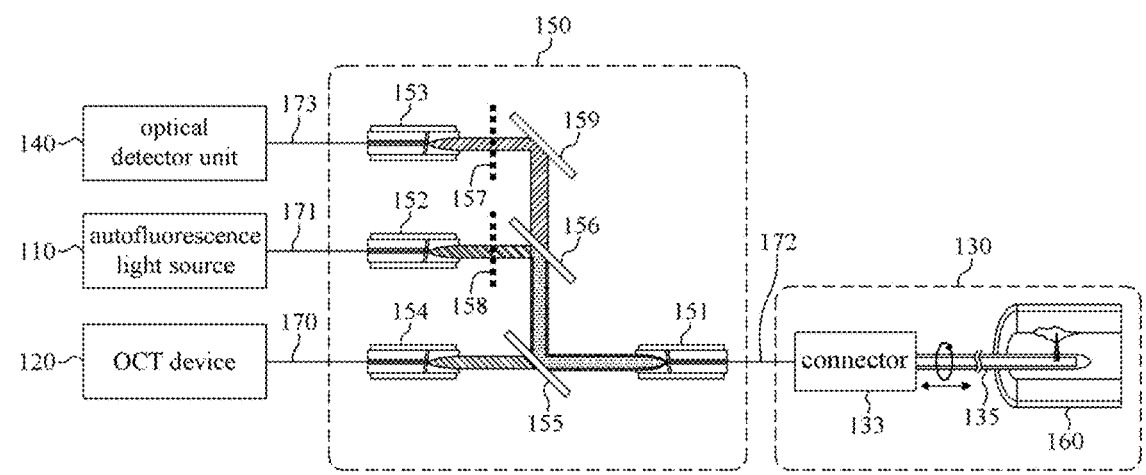
FIG. 1 illustrates an imaging catheter system according to an embodiment of the present disclosure.

As the disclosure allows for various changes and numerous embodiments, particular embodiments will be illustrated in the drawings and described in detail in the written description. However, this is not intended to limit the present disclosure to particular modes of practice, and it is to be appreciated that all changes, equivalents, and substitutes that do not depart from the spirit and technical scope of the present disclosure are encompassed in the present disclosure. In describing the drawings, similar reference numerals are used for similar elements.

Certain embodiments of the present disclosure are described below in more detail with reference to the accompanying drawings.

FIG. 1 illustrates an imaging catheter system according to an embodiment of the present disclosure.

Referring to FIG. 1, an imaging catheter system according to an embodiment of the present disclosure may include an autofluorescence light source 110, an OCT device 120, a catheter device 130, an optical detection unit 140, and a first optics system 150. An imaging catheter system according to an embodiment of the present disclosure may be an imaging catheter system that utilizes optical coherence tomography and autofluorescence lifetime imaging microscopy.

The autofluorescence light source 110 may output light that can allow a sample 160, such as a blood vessel, into which the catheter 133 of the catheter device 130 is inserted, to generate autofluorescence. The wavelength of the light outputted by the autofluorescence light source 110 can be of an ultraviolet region, and in one example, a wavelength of 355 nm can be used.

The first optics system 150 may receive input of the light from the autofluorescence light source 110 and the light of the OCT light source outputted from the OCT device 120 and may provide the light to the catheter device 130. The autofluorescence inputted to the catheter device 130 may be transferred to the optical detection unit 140, and the light of the OCT light source scattered from the sample 160 may be transferred to the OCT device 120. In one example, the light of the OCT light source can have a wavelength of 1250~1350 nm.

The catheter device 130 may receive input of the light from the autofluorescence light source 110 and the light from the OCT light source to scan the sample 160.

The optical detection unit 140 may detect the autofluorescence generated from the sample 160. In one example, the optical detection unit 140 can be a PMT (photomultiplier tube) detector that detects light with very high sensitivity in the ultraviolet, visible ray, and near-infrared regions of an electromagnetic field.

According to an embodiment of the present disclosure, tomographic images of the sample can be generated by way of optical coherence tomography, and the autofluorescence generated from the components of the tissue forming the sample can be imaged by way of autofluorescence lifetime imaging microscopy.

Providing a more specific description of an imaging catheter system based on an embodiment of the present disclosure, the first optics system 150 may include collimators that transfer the light of the light source to the catheter device as well as dichroic mirrors 155, 156 that adjust the path of the light between the collimators. Certain embodiments can further include reflective mirrors 159 and optical filters 157, 158 for increasing the signal-to-noise ratio.

A fourth collimator 154 may receive input of the light of the OCT light source via a single-mode fiber 170 and may transfer the light to a first dichroic mirror 155, and the first dichroic mirror 155 may pass the light from the OCT light source to transfer the light to a first collimator 151.

A second collimator 152 may receive the light from the autofluorescence light source via a multi-mode fiber or single-mode fiber 171 and may transfer the light to the first collimator 151. Here, the light outputted from the second collimator 152 may be reflected by the first and second dichroic mirrors 155, 156 to be transferred to the first collimator 151.

The first collimator 151 may receive input of the light from the autofluorescence light source 110 and OCT light source and may transfer the light to the catheter device 130 via a double-clad fiber 172. Also, the first collimator 151 may transfer the autofluorescence generated from the sample 160 and the light of the OCT light source scattered from the sample 160 towards the first dichroic mirror 155.

The first dichroic mirror 155 may reflect the autofluorescence towards the second dichroic mirror 156 and may pass the light of the OCT light source to transfer it to the fourth collimator 154.

The second dichroic mirror 156 may pass the autofluorescence and transfer it to the reflective mirror 159, and the autofluorescence reflected by the reflective mirror 159 may be inputted to a third collimator 153. That is, the third collimator 153 may receive input of the autofluorescence generated from the sample 160 via the first collimator 151 and may transfer it via a multi-mode fiber 173 to the optical detection unit 140.

The catheter device 130 may include a catheter 133 and an optical connector 131 that connects the catheter 133 with the first collimator 151. The optical connector 131 and the first collimator 151 may be connected with a double-clad fiber 172, and the catheter 133 may be an expendable device that can be readily fastened and separated by way of the optical connector 131. The catheter device 130 may rotate together with the first collimator 151, and the catheter 133 can be inserted into the sample 160 to scan the inside of the sample while rotating or moving back and forth.

The core of a double-clad fiber is made of germanium-doped silica in order to reduce attenuation within the fiber, and germanium-doped silica exhibits an autofluorescent property. A strong autofluorescent property is displayed for wavelengths of the ultraviolet region, but an autofluorescent property is shown not only for the ultraviolet region but also for the visible ray and infrared regions as well.

The autofluorescence generated by the core of a double-clad fiber may act as artifacts with respect to the autofluorescence generated from the sample, becoming noise in the autofluorescence lifetime image. As such, a measure for removing such noise is necessary.

Figure 2A:
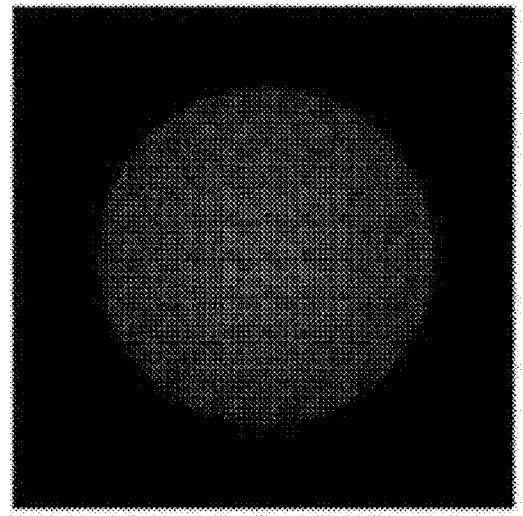
FIG. 2A and FIG. 2B illustrate the profile of an annular beam according to an embodiment of the present disclosure.
Figure 2B:
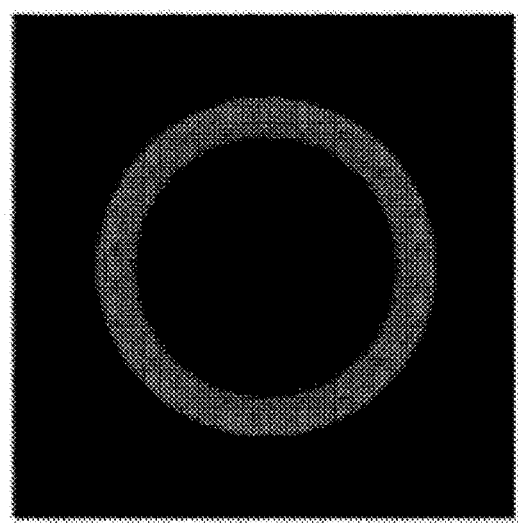

FIG. 2A and FIG. 2B illustrate the profile of an annular beam according to an embodiment of the present disclosure, where FIG. 2A shows the profile of a circular beam, and FIG. 2B shows the profile of an annular beam. In FIG. 2A and FIG. 2B, the relatively brighter portions represent the shapes of the beams.

The parallel beam outputted from the second collimator 152 of FIG. 1 may be a circular beam, such as that shown in FIG. 2A. Therefore, the parallel beam coupled to the double-clad fiber 172 via the first collimator 151 may be coupled also to the core of the double-clad fiber 172, whereby an autofluorescence component may be generated by the core.

Thus, the present disclosure proposes an annular-beam coupling system that can reduce the autofluorescence component generated by the core of the double-clad fiber by coupling an annular beam, such as that shown in FIG. 2B, to the double-clad fiber. Compared to the circular beam of FIG. 2A, the annular beam of FIG. 2B can have the light formed in the shape of a ring in the perimeter portion, so that the annular beam can be coupled to the cladding region without being coupled to the core of the double-clad fiber, resulting in a reduction in the autofluorescence component generated by the core of the double-clad fiber.

An annular-beam coupling system according to an embodiment of the present disclosure can generate an annular beam by converting a parallel beam of a circular shape formed by a collimator into an annular beam or by adjusting the incident angle of the light from the light source entering the multi-mode fiber or double-clad fiber. Alternatively, an annular beam can be generated by using a hollow core fiber, which has a core in an annular form. A more detailed description of certain embodiments is provided below with reference to the accompanying drawings.

An annular-beam coupling system according to an embodiment of the present disclosure can be applied not only to imaging catheter systems that employ optical coherence tomography and autofluorescence lifetime imaging microscopy but to all types of imaging catheter systems in which autofluorescence may be generated in the core of a double-clad fiber. For example, an embodiment of the present disclosure can be applied to imaging catheter systems based on optical coherence tomography and near-infrared fluorescence imaging techniques, imaging catheter systems based on optical coherence tomography and near-infrared spectroscopy techniques, imaging catheter systems based on optical coherence tomography and autofluorescence imaging, etc.

First Embodiment

An annular-beam coupling system according to an embodiment of the present disclosure may include a fiber, a collimator, an annular-beam generation unit, and a double-clad fiber.

The fiber may transfer the light of the light source, and the collimator may receive input of the light outputted from the fiber to form a parallel beam of a circular shape. The annular-beam generation unit may convert the parallel beam into an annular beam, and the annular beam may be coupled to the cladding region of the double-clad fiber.

The fiber may correspond to the multi-mode fiber or single-mode fiber 171 of FIG. 1, while the collimator may correspond to the second collimator 152. Furthermore, the double-clad fiber may correspond to the double-clad fiber 172 of FIG. 1. That is, the annular-beam generation unit according to an embodiment of the present disclosure may be positioned at the output end of the second collimator 152 to convert the parallel beam of the second collimator 152 into an annular beam.

Figure 3:
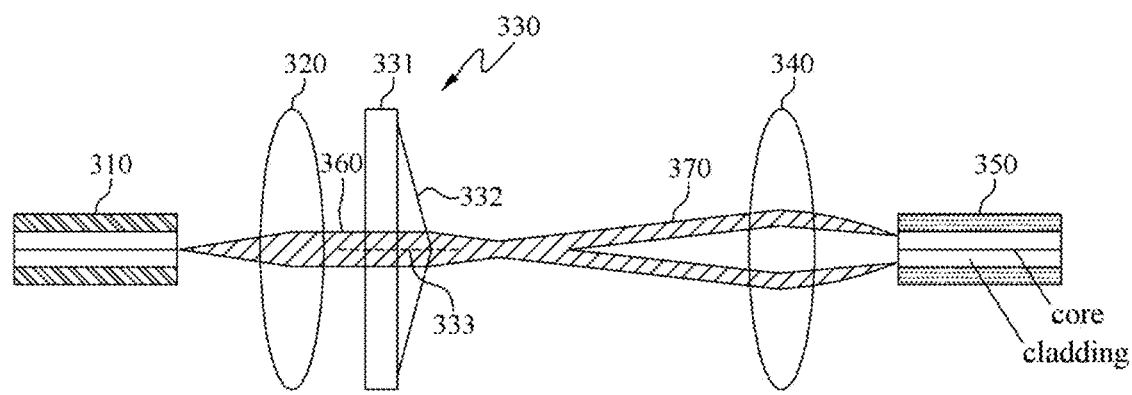
FIG. 3 illustrates an annular-beam coupling system according to a first embodiment of the present disclosure.

FIG. 3 illustrates an annular-beam coupling system according to a first embodiment of the present disclosure. In FIG. 3 and in subsequent figures, collimators are expressed in the form of a lens for convenience.

Referring to FIG. 3, the annular-beam coupling system can use an axicon lens 330 to convert a parallel beam 360 into an annular beam 370. An axicon lens 330 may be formed such that one side has a planar shape and the reverse side protrudes outward in a conical shape. The axicon lens 330 can be arranged such that the central axis 333 of the axicon lens 330 is positioned on the central axis 333 of the parallel beam.

The light outputted from the fiber 310 may be formed into a parallel beam 360 by the collimator 320, and the axicon lens 330 may convert the parallel beam 360 into an annular beam 370. When the parallel beam 360 enters the planar portion 331 of the axicon lens 330, the light may be refracted in the direction of the central axis 333 of the protrusion part 332 of the axicon lens, thereby forming an annular beam 370. The annular beam 370 can be coupled via a collimator 340 to the cladding region of the double-clad fiber 350. Here, the collimator 340 can correspond to the first collimator 151 of FIG. 1.

The angle of the protrusion part of the axicon lens can be varied depending on the diameter of the parallel beam, the distance to the collimator, and the diameter of the double-clad fiber.

Second Embodiment

Figure 4:
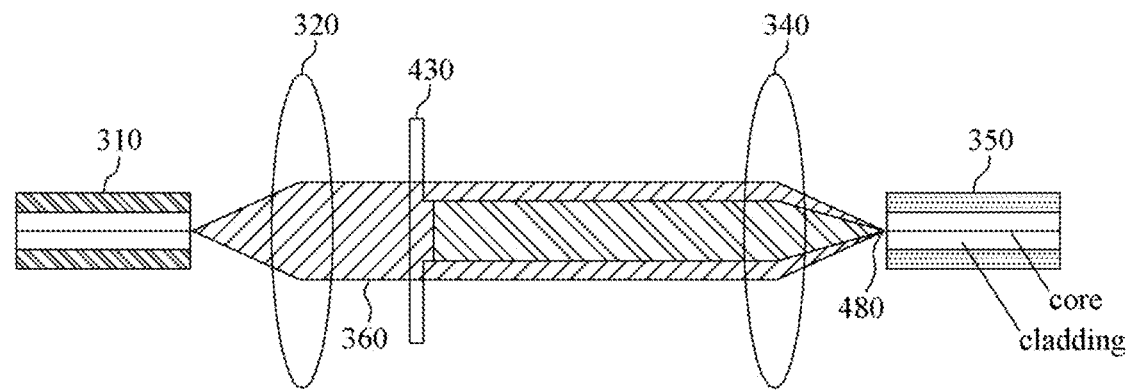
FIG. 4 illustrates an annular-beam coupling system according to a second embodiment of the present disclosure.
Figure 5A:
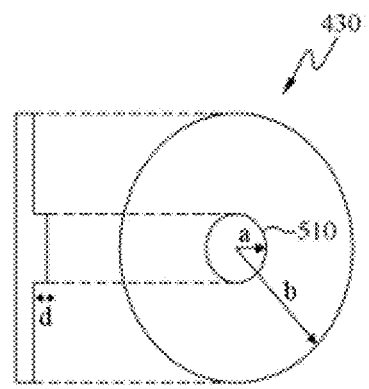
Figure 5A:
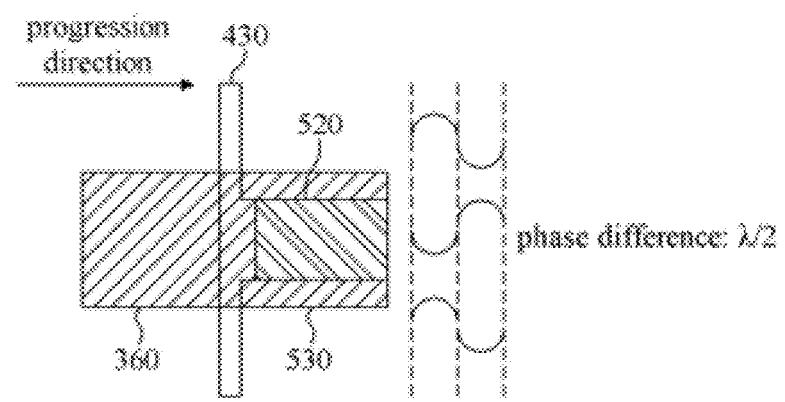
Figure 6:
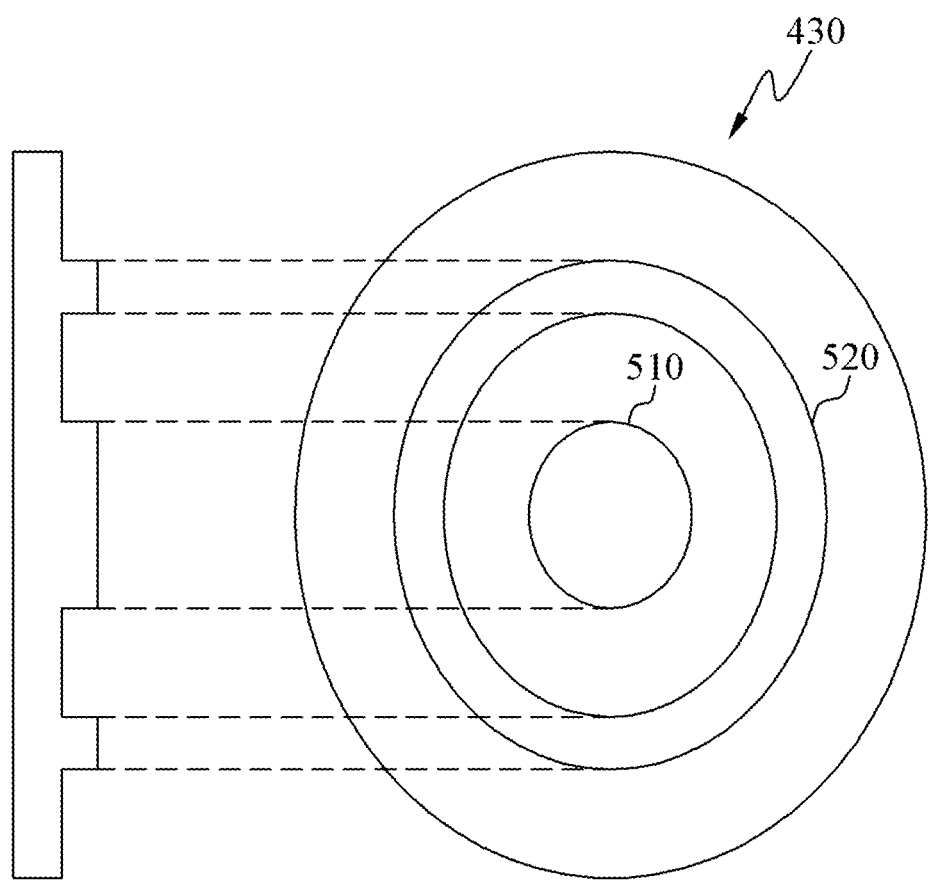

FIG. 4 illustrates an annular-beam coupling system according to a second embodiment of the present disclosure, and FIG. 5A, FIG. 5B and FIG. 6 illustrate examples of a phase spatial filter.

Referring to FIG. 4, the annular-beam coupling system can use a phase spatial filter 430 to convert a parallel beam into an annular beam. A phase spatial filter may be a filter that changes the phase of light passing through the phase spatial filter.

As in FIG. 4, a phase spatial filter 430 may change the phase of the parallel beam outputted from the collimator 320 to convert a parallel beam into an annular beam at the focal position 470.

The phase spatial filter 430 may include a first protrusion part 510, as illustrated in FIG. 5A and FIG. 5B. The first protrusion part 510 may have a shape protruding in the progression direction of the parallel beam 360 or in an opposite direction of the progression direction of the parallel beam 360, and the diameter (a) of the first protrusion part 510 may be smaller than the diameter of the parallel beam 360. In other embodiments, the phase spatial filter 430 may further include a second protrusion part 520 of an annular shape that protrudes in the progression direction of the parallel beam 360 or the opposite direction of the progression direction of the parallel beam 360 at a position separated from the first protrusion part 510 by a preset distance, as illustrated in FIG. 6.

The phase spatial filter 430, including the first protrusion part 510, can be made from a material of a first refractive index, such as epoxy, and the light that passes through the phase spatial filter 430 may pass through a material of a second refractive index, such as air. The light 520 passing through the first protrusion part 510 may, compared to the light 530 passing through the region outside the first protrusion part 510, pass through more of the material having the first refractive index by an amount corresponding to the height (d) of the first protrusion part 510, and consequently, a phase difference may be generated in the parallel beam 360 between the light 520 that has passed through the first protrusion part 510 and the light 530 that has not, as illustrated in FIG. 5B.

Depending on the height (d) of the first protrusion part 510, a phase difference of $\lambda/2$ can be generated between the light 520 that has passed through the first protrusion part 510 and the light 530 that has not, and an annular beam can be formed due to destructive interference at the focal position 480 where the light passing through the phase spatial filter 430 is focused.

The height (d) of the first protrusion part 510 can be determined based on the difference between the first refractive index ($n_1$) and the second refractive index ($n_2$) and the wavelength ($\lambda$) of the parallel beam 360; for example, the height (d) of the first protrusion part 510 can be determined as in [Equation 1].

$$d = \frac{\lambda}{2|n_1 - n_2|} \qquad \text{[Equation 1]}$$

Also, the diameter (a) of the first protrusion part 510 can be varied according to the diameter of the parallel beam 360 formed, such as to satisfy the condition for destructive interference, and as the diameter of the parallel beam 360 is increased, the diameter (a) of the first protrusion part 510 can also be increased.

Third Embodiment

Figure 7:
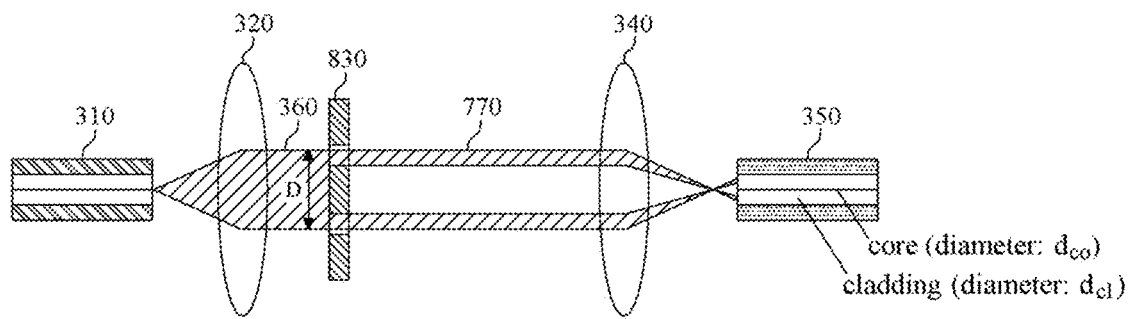
FIG. 7 illustrates an annular-beam coupling system according to a third embodiment of the present disclosure.
Figure 8:
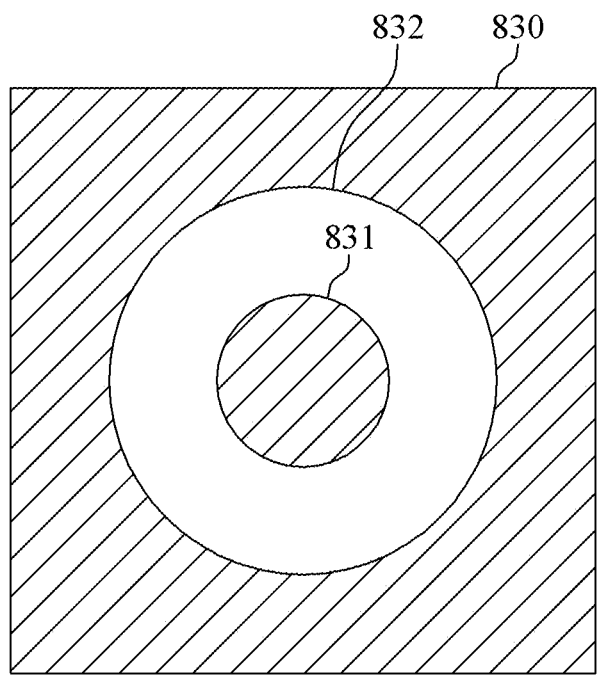
FIG. 8 illustrates an annular filter (annular aperture) used in FIG. 7.
Figure 9:
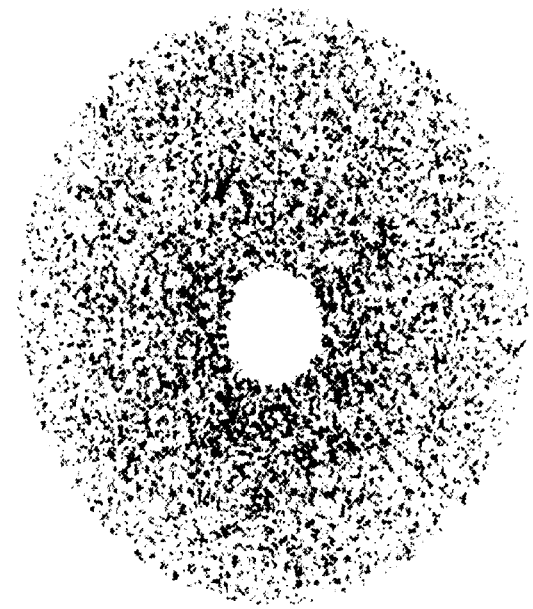
FIG. 9 illustrates simulation results for an annular beam using an annular filter.

FIG. 7 illustrates an annular-beam coupling system according to a third embodiment of the present disclosure, and FIG. 8 illustrates an annular filter (annular aperture) used in FIG. 7. Also, FIG. 9 illustrates simulation results for an annular beam using an annular filter.

As in FIG. 7, an annular filter 830 may convert a parallel beam outputted from the collimator 320 into an annular beam.

An annular filter 830 according to an embodiment of the present disclosure may include an optical absorption part 831, which may have a circular shape and may absorb a portion of the parallel beam 360, and an annular aperture 832, which may surround the optical absorption part 831 and pass a portion of the parallel beam 360. The optical absorption part 831 can be made from a material that absorbs light and, in one example, can include a cobalt component.

The center portion of the parallel beam 360 may be blocked by the optical absorption part 831, and only the perimeter region of the parallel beam 360 may be passed by the annular aperture 832, whereby an annular beam 770 can be formed. To this end, the diameter of the optical absorption part 831 can be designed to be smaller than the diameter (D) of the parallel beam 360.

If the diameter of the annular aperture 832 is smaller than the diameter (D) of the parallel beam 360, then a portion of the parallel beam 360 can be unnecessarily blocked at the annular filter 830; therefore, it may be preferable that the diameter of the annular aperture 832 be greater than the diameter (D) of the parallel beam 360.

The ratio of the diameter of the optical absorption part 831 to the diameter (D) of the parallel beam 360 (first ratio) can be designed to be greater than or equal to the ratio of the diameter ($d_{co}$) of the core to the diameter ($d_{cl}$) of the cladding in the double-clad fiber 350 (second ratio), where the smaller the difference between the first ratio and the second ratio, the smaller the optical loss by the optical absorption part 831.

In other words, unlike the other embodiments, the third embodiment may form the annular beam with a loss of a portion of the parallel beam 360 created by the optical absorption part 831, so that there is a need for minimizing the optical loss by the optical absorption part 831, and if the diameter of the optical absorption part 831 is excessively large compared to the diameter of the core of the double-clad fiber, the optical loss by the optical absorption part 831 may be increased. That is, if the diameter of the optical absorption part 831 is made larger than the minimum diameter for the optical absorption part 831 that can prevent a coupling of the annular beam to the core of the double-clad fiber, then unnecessary optical loss may be generated.

Conversely, if the diameter of the optical absorption part 831 is excessively small compared to the diameter of the core of the double-clad fiber, the annular beam can be coupled to the core of the double-clad fiber.

Therefore, in the third embodiment, the first ratio can be made greater than the second ratio so as to prevent the annular beam from being coupled to the core of the double-clad fiber while minimizing the difference between the first ratio and the second ratio so as to minimize the optical loss by the optical absorption part 831.

Also, in order that the focal position of the annular beam may be formed on the cladding of the double-clad fiber, the distance between the double-clad fiber 350 and the collimator 340 can be shortened or extended by a preset amount compared to cases that do not use an annular beam.

FIG. 9 shows the simulation result of the shape of an annular beam coupled to a double-clad fiber according to third embodiment, provided using simulation software. In FIG. 9, the region formed by black dots represents the shape of the annular beam.

FIG. 9 shows the result of a simulation when the diameter of the optical absorption part 831 is set to 150 μm, the diameter of the annular aperture 832 is set to 3 mm, the diameter ($d_{co}$) of the core of the double-clad fiber 350 is set to 10 μm, the diameter ($d_{cl}$) of the cladding is set to 105 μm, and the diameter of the parallel beam is set to 1.5 mm.

In this case, the ratio of the diameter of the optical absorption part 831 to the diameter (D) of the parallel beam is 0.1 (150/1500), and the ratio of the core diameter ($d_{co}$) to the cladding diameter ($d_{cl}$) of the double-clad fiber is 0.095. Therefore, the annular beam of the FIG. 9 would not be coupled to the core of the double-clad fiber, and the optical loss by the optical absorption part 831 would not be great.

Fourth Embodiment

Figure 10:
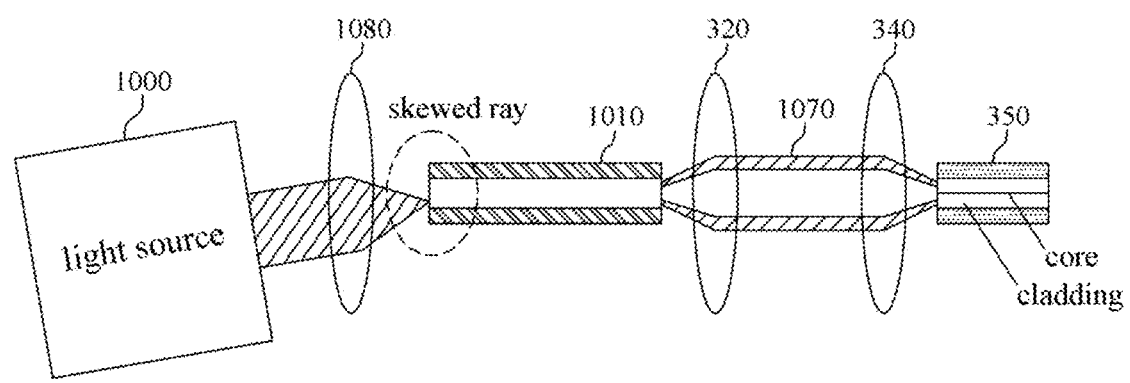
FIG. 10 illustrates an annular-beam coupling system according to a fourth embodiment of the present disclosure.
Figure 11A:
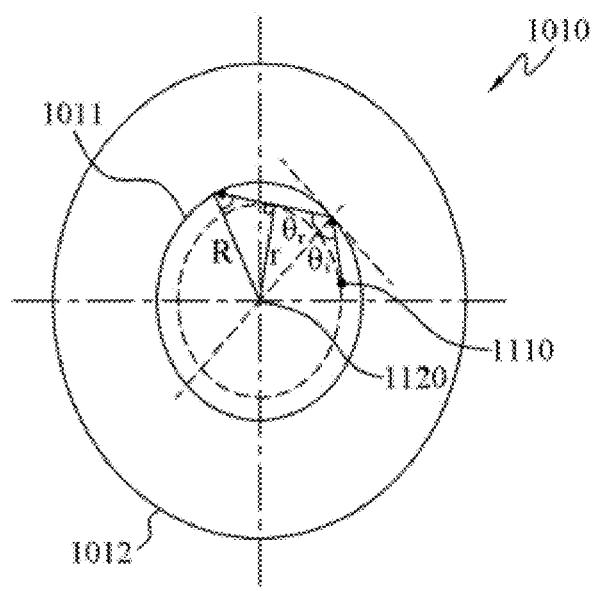
FIG. 11A and FIG. 11B illustrate the principles for forming a skewed ray.
Figure 11B:
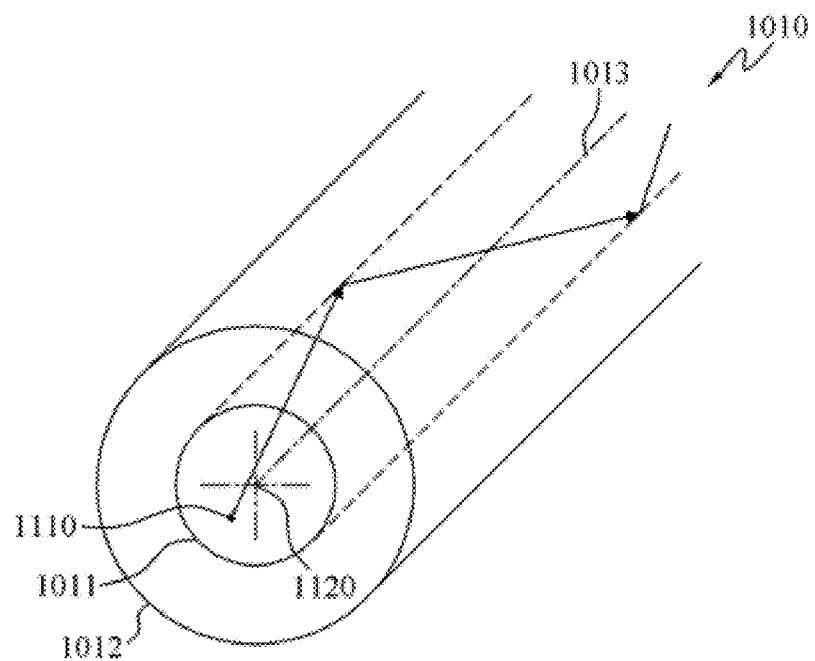

FIG. 10 illustrates an annular-beam coupling system according to a fourth embodiment of the present disclosure, and FIG. 11A and FIG. 11B illustrate the principles for forming a skewed ray.

Unlike the first to third embodiments described above, the fourth embodiment does not use an annular beam but instead uses a skewed ray. A skewed ray refers to light that enters at an incline when the light is coupled to the optical fiber, such that the light is guided without passing through the center of the optical fiber.

Referring to FIG. 11A and FIG. 11B, the light from the light source 1000 may enter the multi-mode fiber 1010 via a lens 1080. Here, the light of the light source 1000 may enter the multi-mode fiber 1010 such that the light is guided through the perimeter region of the core, separated by a preset distance from the center of the multi-mode fiber 1010. That is, the light guided in the multi-mode fiber 1010 may form a skewed ray. Thus, the shape of the beam outputted from the multi-mode fiber 1010 can have an annular shape, and such annular beam may be coupled to the cladding of the double-clad fiber 350.

While it is not illustrated in FIG. 11A and FIG. 11B, the annular-beam coupling system can further include an actuator or an optics system.

The actuator may adjust the position of the light source 1000, as in FIG. 11A and FIG. 11B for example, such that the light from the light source 1000 is guided in the perimeter region of the multi-mode fiber 1010. As the position of the light source 1000 is adjusted, the incident angle or the direction of incidence of the light of the light source 1000 with respect to the multi-mode fiber 1010 can be adjusted.

The optics system, from between the light source and the multi-mode fiber, may adjust the path of the light from the light source 1000 such that the light of the light source 1000 is guided in the perimeter region of the core. That is, the position of the light source 1000 may be fixed, and the path of the light from the light source can be adjusted so as to adjust the incident angle or the direction of incidence of the light of the light source with respect to the multi-mode fiber 1010.

A more detailed description of the skewed ray is provided below with reference to FIG. 11A and FIG. 11B. In FIG. 11A and FIG. 11B, the arrows represent the progression direction of the light.

In FIG. 11A, which shows a cross section of the multi-mode fiber 1010, the light is inputted at a point 1110 that is separated by a preset distance from the central axis 1120 of the multi-mode fiber's core 1011. Here, the light may not enter along a direction parallel to the lengthwise direction 1013 of the multi-mode fiber 1010 but rather may enter inclined at a preset angle with respect to the lengthwise direction 1013, i.e. the central axis 1120, of the multi-mode fiber 1010 in the direction of the cladding 1012, as illustrated in FIG. 11A and FIG. 11B, which shows an angled view of the arrangement. The light from the light source 1000 can be made to enter with an incline of a preset angle from the central axis 1120 by way of an actuator or an optics system.

Here, as the light enters the multi-mode fiber 1010 at an incident angle $\theta_i$ that is an angle greater than or equal to a threshold angle, then the reflection angle $\theta_r$ may be equal to the incident angle, and total reflection may occur within the core 1011, whereby the light may progress along the lengthwise direction 1013 of the multi-mode fiber 1010. Due to such total reflection, the light can be guided only within the perimeter region of the core 1011 separated by a preset distance (r) from the central axis 1120 of the multi-mode fiber 1010, and a skewed ray can be formed.

Fifth Embodiment

Figure 12:
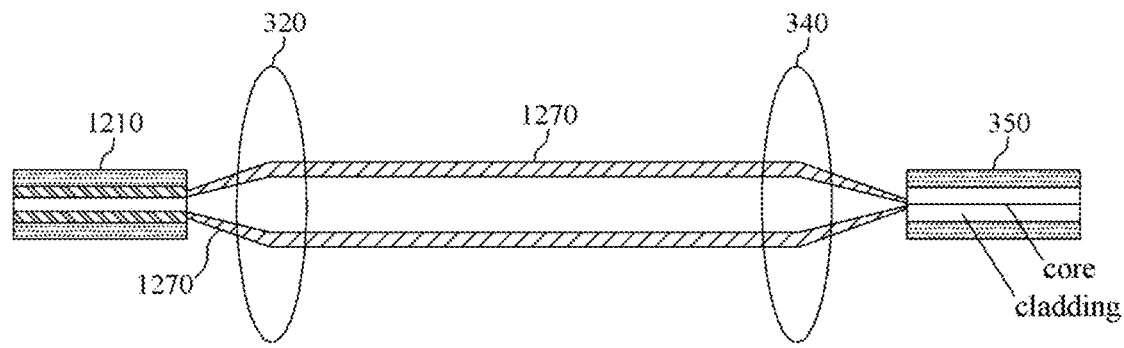
FIG. 12 illustrates an annular-beam coupling system according to a fourth embodiment of the present disclosure.
Figure 13:
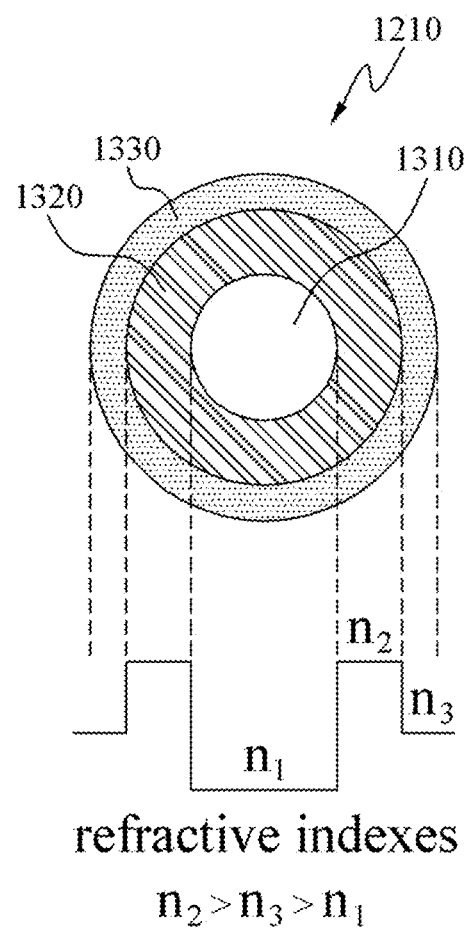
FIG. 13 illustrates the structure and refractive index profiles of a hollow core fiber.

FIG. 12 illustrates an annular-beam coupling system according to a fourth embodiment of the present disclosure, and FIG. 13 illustrates the structure and refractive index profiles of a hollow core fiber.

In the fifth embodiment, unlike in the first to fourth embodiments, the annular beam may be formed by using the structure of the fiber itself.

Referring to FIG. 12, the annular-beam coupling system may include a light source, a hollow core fiber 1210 that receives input of the light of the light source and outputs an annular beam 1270, and a double-clad fiber 350 that has the annular beam 1270 coupled to the cladding region. That is, in FIG. 12 a hollow core fiber may be used instead of a single-mode fiber or multi-mode fiber, where the hollow core fiber 1210 may, as illustrated in FIG. 13, include an annular core 1320 and cladding 1330, with the center portion 1310 of the hollow core fiber 1210 empty. In order that light may be guided through the annular core 1320, the refractive index characteristics of the hollow core fiber 1210 may be such that the refractive index of the core ($n_2$), the refractive index of the cladding ($n_3$), and the refractive index of the center portion ($n_1$) decrease in said order.

Thus, since light can be guided in the core 1320 of the hollow core fiber 1210, and since the core 1320 has an annular shape, an annular beam 1270 can be outputted from the hollow core fiber 1210.

While the present disclosure is described above by way of limited embodiments and drawings that refer to particular details such as specific elements, etc., these are provided only to aid the general understanding of the present disclosure. The present disclosure is not to be limited by the embodiments above, and the person having ordinary skill in the field of art to which the present disclosure pertains would be able to derive numerous modifications and variations from the descriptions and drawings above. Therefore, it should be appreciated that the spirit of the present disclosure is not limited to the embodiments described above. Rather, the concepts set forth in the appended scope of claims as well as their equivalents and variations are encompassed within the spirit of the present disclosure.

What is claimed is:

1. An annular-beam coupling system comprising:
a fiber configured to transfer light from a light source;
a collimator configured to receive the light outputted from the fiber and form a parallel beam of a circular shape;
an annular-beam generation unit configured to convert the parallel beam into an annular beam; and
a double-clad fiber configured to have the annular beam coupled to a cladding region thereof,
wherein the annular-beam generation unit comprises a phase spatial filter, and
wherein the phase spatial filter comprises a first protrusion part, the first protrusion part having a shape protruding in a progression direction of the parallel beam or an opposite direction of the progression direction, the first protrusion part having a diameter thereof smaller than a diameter of the parallel beam.

2. The annular-beam coupling system of claim 1, wherein the phase spatial filter further comprises a second protrusion part, the second protrusion part separated from the first protrusion part by a preset distance and protruding in the progression direction or the opposite direction of the progression direction.

3. The annular-beam coupling system of claim 1, wherein a diameter of an annular aperture is greater than a diameter of the parallel beam.

4. An annular-beam coupling system comprising:
a light source;
a multi-mode fiber configured to guide light from the light source; and
a double-clad fiber configured to have an annular beam coupled to a cladding region thereof, the annular beam outputted from the multi-mode fiber,
wherein the light from the light source enters the multi-mode fiber to be guided in a perimeter region of a core, the perimeter region separated from a central axis of the multi-mode fiber by a preset distance, and
wherein the light from the light source is guided by way of total reflection.

5. The annular-beam coupling system of claim 4, further comprising an actuator configured to adjust a position of the light source such that the light from the light source is guided in the perimeter region.

6. The annular-beam coupling system of claim 5, wherein the actuator adjusts the position of the light source such that the light from the light source enters inclined at a preset angle with respect to the central axis.

7. The annular-beam coupling system of claim 4, further comprising an optics system configured to adjust a path of the light from the light source between the light source and the multi-mode fiber such that the light from the light source is guided in the perimeter region.

* * * * *